(12) United States Patent
Gralla et al.

(10) Patent No.: US 8,618,315 B2
(45) Date of Patent: Dec. 31, 2013

(54) METHOD FOR PRODUCING 2-SUBSTITUTED TETRAHYDROPYRANOLS

(75) Inventors: Gabriele Gralla, Mannheim (DE); Ralf Pelzer, Fürstenberg (DE); Klaus Ebel, Lampertheim (DE); Ulrich Griesbach, Mannheim (DE); Jörg Botzem, Limburgerhof (DE)

(73) Assignee: BASF SE (DE)

( * ) Notice: Subject to any disclaimer, the term of this patent is extended or adjusted under 35 U.S.C. 154(b) by 5 days.

(21) Appl. No.: 13/321,417

(22) PCT Filed: May 11, 2010

(86) PCT No.: PCT/EP2010/056403
§ 371 (c)(1),
(2), (4) Date: Nov. 18, 2011

(87) PCT Pub. No.: WO2010/133473
PCT Pub. Date: Nov. 25, 2010

(65) Prior Publication Data
US 2012/0059177 A1    Mar. 8, 2012

(30) Foreign Application Priority Data
May 19, 2009  (EP) .................................. 09160665

(51) Int. Cl.
*C07D 309/10*    (2006.01)
(52) U.S. Cl.
USPC ........................................................ 549/423
(58) Field of Classification Search
USPC ........................................................ 549/423
See application file for complete search history.

(56) References Cited

FOREIGN PATENT DOCUMENTS

| EP | 1493737 A1 | 1/2005 |
|---|---|---|
| EP | 1516879 A1 | 3/2005 |
| JP | 2007-154609 A * | 6/2007 |
| JP | 2007154069 A | 6/2007 |
| SU | 825528 A1 | 4/1981 |

OTHER PUBLICATIONS

Kawanobe, Machine translation of Detailed Description of JP 2007-154609 A (2007).*
DeSilva, Essentials of Ion Exchange, 9presented at the 25th Annual WQA Conference( Mar. 17,1999) (from the Internet).*
Definition of Ion Exchange Resins, from the Great Soviet Encyolpedia (1979) (from the Internet).*
Tyman, Thetrahedron Letter No. 51, 1970, pp. 4507-4508.
Ibatullin, Chemistry of Heterocyclic Compounds, vol. 25, 1989, pp. 1107-1109.
Thomson Scientific, London, 2007-564955.
Thomson Scientific, London, 1982-11549E.
Gevorkyan et al., Chemistry of Heterocyclic Compounds, no. 12, 1982, pp. 1240-1242.
International Search Report for PCT/EP2010/056403.
Translation of the International Preliminary Report on Patentability for PCT/EP2010/056403 dated Nov. 29, 2011.

* cited by examiner

*Primary Examiner* — Bernard Dentz
(74) *Attorney, Agent, or Firm* — Novak Druce Connolly Bove + Quigg LLP

(57) ABSTRACT

The present invention relates to a process for the preparation of 2-substituted 4-hydroxy-4-methyltetrahydropyranols by reacting 3-methylbut-3-en-1-ol (isoprenol) with the corresponding aldehydes in the presence of a strongly acidic cation exchanger. Specifically, the present invention relates to a corresponding process for the preparation of 2-isobutyl-4-hydroxy-4-methyltetrahydropyran by reacting isoprenol with isovaleraldehyde.

15 Claims, No Drawings

METHOD FOR PRODUCING 2-SUBSTITUTED TETRAHYDROPYRANOLS

CROSS-REFERENCE TO RELATED APPLICATIONS

This application is a national stage application (under 35 U.S.C. §371) of PCT/EP2010/056403, filed May 11, 2010, which claims benefit of EP 09160665.7, filed May 19, 2009.

BACKGROUND OF THE INVENTION

The present invention relates to a process for the preparation of 2-substituted 4-hydroxy-4-methyltetrahydropyranols by reacting 3-methylbut-3-en-1-ol (isoprenol) with the corresponding aldehydes in the presence of a strongly acidic cation exchanger. Specifically, the present invention relates to a corresponding process for the preparation of 2-isobutyl-4-hydroxy-4-methyltetrahydropyran by reacting isoprenol with isovaleraldehyde.

Tetrahedron Letters No. 51, pages 4507-4508, 1970 describes the reaction of 3-alken-1-ols with aldehydes and their use for producing the aroma chemicals rose oxide and dihydrorose oxide. Also mentioned here is the reaction of 3-methylbutanal with isoprenol under acidic conditions.

Chemistry of Heterocyclic Compounds, pages 1107-1109, 1990 describes the condensation of isoprenol with various aldehydes and ketones to give the corresponding di- and tetrahydropyrans in the presence of silica gel or $Al_2O_3$ under solvent-free conditions. Pyranols are obtained here only to a low degree when using $Al_2O_3$.

SU 825 528 discloses a process for the preparation of di- and tetrahydropyrans and tetrahydropyranols by reacting 2-methylbuten-1-o1-4 (isoprenol) with aldehydes or ketones in the presence of an acidic catalyst, where the acidic catalyst is used in an amount of from 0.0001 to 0.01% by weight, based on the amount of isoprenol, and the reaction is carried out at a temperature of from 0 to 25° C. in an organic solvent. The catalysts specified are the ion exchange resin KU-2 (sulfonated polystyrene resin), para-toluene sulfonic acid, sulfuric acid, phosphoric acid or perchloric acid. By way of example, the reaction of isoprenol with isobutyraldehyde in the presence of KU-2, inter alia, is described.

EP 1 493 737 A1 discloses a process for the preparation of mixtures of ethylenically unsaturated 4-methyl- and 4-methylenepyrans and the corresponding 4-hydroxypyrans by reacting the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydrogenation of said mixtures to give the desired ethylenically unsaturated pyrans. Suitable catalysts specified for the first reaction step are mineral acids, such as hydrochloric acid or sulfuric acid, but preferably methanesulfonic acid or para-toluene sulfonic acid.

EP 1 516 879 A1 discloses a process for the preparation of ethylenically unsaturated 4-methyl- and 4-methylenepyrans by reacting a corresponding aldehyde with isoprenol under dehydrogenating conditions, where the amount of water in the reactor is up to 0.25% by weight, while the conversion of the starting compound used in deficit is less than 50%. The catalysts specified as being suitable for this are likewise mineral acids, such as hydrochloric acid or sulfuric acid, but preferably methane sulfonic acid or para-toluenesulfonic acid.

JP 2007-154069 relates to 2-substituted 4-hydroxy-4-methyltetrahydropyranols with a content of the cis-diastereomer of from 70 to 95% by weight. Moreover, the document discloses a process for the preparation of same, by reacting isoprenol with a corresponding aldehyde in the presence of an aqueous solution of an acidic catalyst. Here, the reaction has to be carried out at a concentration of the aqueous catalyst solution either in the range from 1:10% by weight at a temperature of from 0 to 100° C., or in the region of 10% by weight or above at a temperature of from 0 to 30° C. The possible acidic catalysts mentioned are generally also ion exchange resins.

DETAILED DESCRIPTION OF THE INVENTION

Starting from this prior art, the object of the present invention was to provide a process for the preparation of 2-substituted 4-hydroxy-4-methyltetrahydropyrans, specifically 2-isobutyl-4-hydroxy-4-methyltetrahydropyran, which makes the desired compounds accessible as far as possible
- starting from readily available, inexpensive starting materials,
- using readily available, inexpensive reagents
- in an operationally advantageous manner,
- on an industrial scale,
- in a high yield,
- in a high diastereomer excess,
- with the lowest possible formation of undesired by-products that have to be disposed of and
- with as far as possible advantageous odorous properties.

Surprisingly, the object was achieved according to the invention through the provision of a process for the preparation of 2-substituted 4-hydroxy-4-methyltetrahydropyrans of the formula (I)

where the radical
$R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms,
comprising the reaction of 3-methylbut-3-en-1-ol of the formula (II)

with an aldehyde of the formula (III)

where the radical $R^1$ has the same meaning as in formula (I) and
where the reaction is carried out in the presence of water and in the presence of a strongly acidic cation exchanger.

Suitable starting materials for carrying out the process according to the invention are 3-methylbut-3-en-1-ol (isoprenol) of the formula (II),

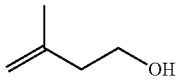
(II)

which is readily accessible by known processes from isobutene and formaldehyde on any scale and is commercially readily available. No particular requirements are placed on the purity, quality or preparation process of the isoprenol to be used according to the invention. It can be used as starting material in the course of the process according to the invention in standard commercial quality and purity with good success. Preference is given to using isoprenol which has a purity of 90% by weight or above, particularly preferably one with a purity of from 95 to 100% by weight and very particularly preferably one with a purity of from 97 to 99.9% by weight or even more preferably 98 to 99.8% by weight.

A further suitable starting material for carrying out the process according to the invention is an aldehyde of the formula (III)

$$R^1—CHO \quad (III),$$

where the radical $R^1$ may be a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms. Here, the term alkenyl radical is to be understood as meaning a hydrocarbon radical which, besides single bonds, also has one or more, preferably 1 to 3, particularly preferably 1 or 2 and very particularly preferably one, ethylenic double bond.

An alkyl substituent is preferably to be understood as meaning one which has 1 to 6 carbon atoms, such as, for example, methyl, ethyl, n-propyl, isopropyl, n-butyl, sec-butyl, Cert-butyl, n-pentyl or n-hexyl, preferably methyl, ethyl, n-propyl, isopropyl, isobutyl.

An alkoxy substituent is preferably to be understood as meaning one which has 1 to 6 carbon atoms, particularly preferably 1 to 3 carbon atoms, such as, for example, methoxy, ethoxy, n-propyloxy, isopropyloxy.

Aldehydes of the formula (III) preferred according to the invention are those in which the radical $R^1$ is a straight-chain or branched alkyl or alkenyl radical having 1 to 12 carbon atoms, or an optionally alkyl- and/or alkoxy-substituted aryl radical having in total 6 to 12 carbon atoms. According to the invention, very particularly preferred aldehydes of the formula (III) are those in which the radical $R^1$ is a straight-chain or branched alkyl or alkenyl radical having 1 to 12 carbon atoms or preferably having 1 to 6 carbon atoms, or is an aryl radical having in total 6 carbon atoms, i.e. is phenyl. Particularly preferred aldehydes of the formula (III) are those in which the radical $R^1$ is a straight-chain or branched alkyl or alkenyl radical having 1 to 12 carbon atoms, very particularly preferably having 1 to 6 carbon atoms. According to the invention, preferred meanings for the radical $R^1$ are therefore, for example, methyl, ethyl, n-propyl, isopropyl, n-butyl, isobutyl, n-pentyl, n-hexyl, n-heptyl, preferably methyl, ethyl, n-propyl, isopropyl, n-butyl, isobutyl, very particularly preferably isobutyl. As aldehydes of the formula (III) accordingly to be used preferably according to the invention, the following may be mentioned: acetaldehyde, valeraldehyde, isovaleraldehyde, pentanal, hexanal, heptanal, benzaldehyde, citral, citronellal. Aldehydes of the formula (III) to be used very particularly preferably according to the invention are therefore isovaleraldehyde and benzaldehyde, in particular isovaleraldehyde.

Within the context of a preferred embodiment, the present invention therefore relates to a process for the preparation of 2-isobutyl-4-hydroxy-4-methyltetrahydropyran of the formula (Ia)

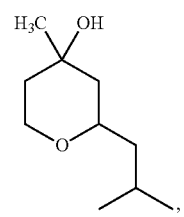
(Ia)

comprising the reaction of 3-methylbut-3-en-1-ol of the formula (II) with isovaleraldehyde of the formula (IIIa)

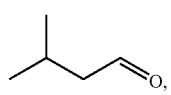
(IIIa)

where the reaction is carried out in the presence of water and in the presence of a strongly acidic cation exchanger.

Within the context of a further, likewise preferred embodiment, the present invention relates to a process for the preparation of 2-phenyl-4-hydroxy-4-methyltetrahydropyran of the formula (Ia')

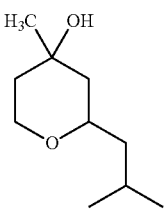
(Ia')

comprising the reaction of 3-methylbut-3-en-1-ol of the formula (II) with benzaldehyde, where the reaction is carried out in the presence of water and in the presence of a strongly acidic cation exchanger.

The starting materials isoprenol and the aldehyde of the formula (III) selected in each case to be used in the course of the process according to the invention can be reacted together in various quantitative ratios. Thus, it is possible to use one of the two starting materials in excess, in which case the level of the selected excess should vary within operationally and economically advantageous limits, but otherwise can in principle be freely chosen. Following the stoichiometry of the reaction according to the invention of isoprenol with the selected aldehyde of the formula (III), isoprenol and the aldehyde of the formula (III), preferably isovaleraldehyde, are used in a molar ratio in the range from 1:2 to 2:1, corresponding to a double molar excess of one of the starting materials. Within the context of a preferred embodiment, the process according to the invention is carried out in such a way that isoprenol and the aldehyde of the formula (III) are used in a molar ratio of from 0.7:1 to 2:1. The process according to the invention is particularly preferably carried out in such a way that isoprenol and the aldehyde of the formula (III) are used in a molar ratio of from 1:1 to 2:1. The process according to the invention is very particularly preferably carried out in such a way that isoprenol and the aldehyde of the formula (III) are used in a molar ratio of from 1:1 to 1.5:1.

The reaction of isoprenol with the selected aldehyde of the formula (III), preferably with isovaleraldehyde, that is to be carried out in the course of the process according to the invention for the preparation of the 2-substituted 4-hydroxy-4-methyltetrahydropyrans of the formula (I), preferably for the preparation of 2-isobutyl-4-hydroxy-4-methyltetrahydropyran of the formula (Ia), is carried out in the presence of water. This means that besides isoprenol, the aldehyde of the formula (III) and the selected strongly acidic cation exchanger, water is also added to the reaction mixture. In addition, the reaction mixture can also comprise small amounts of water which can be released by the dehydration of the desired process product of the formula (I) which possibly takes place as an undesired secondary reaction.

The reaction of the isoprenol with the selected aldehyde of the formula (III) is usually carried out in the presence of about at least 10 mol % of water, where the amount of water refers to the amount of the starting material isoprenol, used optionally in deficit, or to the aldehyde of the formula (III), or, in the case of the equimolar reaction of the two starting materials, to the quantitative amount of one of the two.

Above the stated value, the amount of water can be freely chosen and is limited only by processing or cost aspects, if at all, and can be used perfectly well in a large excess, for example in 10- to 100-fold excess or even more. Preferably, a mixture of isoprenol and the selected aldehyde of the formula (III), preferably isovaleraldehyde, is prepared with the selected amount of water such that the added water remains dissolved in the mixture of isoprenol and the selected aldehyde, i.e. no two-phase system is present.

Usually, in the course of the process according to the invention, the starting materials isoprenol and the selected aldehyde of the formula (III) are reacted in the presence of at least 25 mol %, preferably of at least 50 mol %, even more preferably of at least 75 and even more preferably of at least 90 to about 1000 mol %, of water, where the amount of water refers to the amount of the starting material isoprenol, used optionally in deficit, or to the aldehyde of the formula (III), or, in the case of the equimolar reaction of the two starting materials, to the quantitative amount of one of the two.

Within the context of a preferred embodiment, the reaction to be carried out according to the invention is carried out such that it is carried out in the presence of an at least equimolar amount of water, where the amount of water refers to the amount of the starting material isoprenol, used optionally in deficit, or to the aldehyde of the formula (III), or, in the case of the equimolar reaction of the two starting materials, to the quantitative amount of one of the two. Consequently, the reaction according to the invention of isoprenol with the selected aldehyde of the formula (III) is preferably carried out in the presence of from 100 to 250 mol %, particularly preferably 100 to 230 mol %, even more preferably 100 to 200 mol % and most preferably in the presence of from 100 to 180 mol %, of water, where the amount of water refers to the amount of the starting material isoprenol, used optionally in deficit, or to the aldehyde of the formula (III), or, in the case of the equimolar reaction of the two starting materials, to the quantitative amount of one of the two.

The specified starting materials, i.e. isoprenol and the aldehyde selected in each case and the water to be used in the above amount can be brought into contact with one another or be mixed in any desired order. Usually, a mixture of isoprenol and the selected aldehyde of the formula (III) is prepared with the selected amount of water and this mixture is used in the course of the reaction to be carried out according to the invention.

The reaction of isoprenol with the selected aldehyde of the formula (III) to be carried out in the course of the process according to the invention for preparing the desired 2-substituted 4-hydroxy-4-methyltetrahydropyrans of the formula (I), is also carried out in the presence of a strongly acidic cation exchanger. Within the context of the present invention, the term strongly acidic cation exchanger is to be understood as meaning those cation exchangers in the H+ form which have strongly acidic groups, usually sulfonic acid groups, whose matrix may be gel-like or macroporous.

One preferred embodiment of the process according to the invention is accordingly one in which a strongly acidic cation exchanger comprising or having sulfonic acid groups is used.

Strongly acidic cation exchangers are in particular ion exchanger resins in the H(+) form. Suitable examples of such are:

strongly acidic ion exchangers (such as e.g. Amberlyst, Amberlite, Dowex, Lewatit, Purolite, Serdolit), which are based on polystyrene, and which comprise copolymers of styrene and divinylbenzene as carrier matrix with sulfonic acid groups in the H(+) form, ion exchanger groups functionalized with sulfonic acid groups ($-SO_3H$).

The ion exchangers differ in the structure of their polymer backbones, and a distinction is made between gel-like and macroporous resins. The strongly acidic ion exchanger resins are generally regenerated with hydrochloric acid and/or sulfuric acid.

Nafion® is the Dupont name for perfluorinated polymeric ion exchanger resins. These are perfluorinated ion exchanger materials consisting of fluorocarbon base chains and perfluorinated side chains which comprise sulfonic acid groups. The resins are produced by a copolymerization of perfluorinated, terminally unsaturated and sulfonyl-fluoride-functionalized ethoxylates with perfluoroethene. Nafion® belongs to the gel-like ion exchanger resins. An example of such a perfluorinated polymeric ion exchanger resin which may be mentioned is Nafion® NR-50.

A particularly preferred embodiment of the process according to the invention is one wherein at least one strongly acidic cation exchanger in the H(--) form is used, where the ion exchanger comprises a polymer backbone having sulfonic acid groups and is either gel-like or comprises macroporous resins.

A very particularly preferred embodiment of the process according to the invention is one wherein the ion exchanger is based on a polystyrene backbone with sulfonic acid groups or on a perfluorinated ion exchanger resin with sulfonic acid groups.

The commercially available strongly acidic cation exchangers are known under the trade names Lewatit® (Lanxess), Purolite® (The Purolite Company), Dowex® (Dow Chemical Company), Amberlite® (Rohm and Haas Company), Amberlyst™ (Rohm and Haas Company).

Strongly acidic cation exchangers preferred according to the invention that may be mentioned are, for example: Lewatit® K 1221, Lewatit® K 1461, Lewatit® K 2431, Lewatit® K 2620, Lewatit® K 2621, Lewatit® K 2629, Lewatit® K 2649, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nafion® NR-50.

Within the scope of a preferred embodiment, the reaction of isoprenol with the selected aldehyde of the formula (III) to be carried out according to the invention is carried out in the presence of at least one strongly acidic cation exchanger which is selected from the group of the cation exchangers comprising Lewatit® K 1221, Lewatit® K 2629, Amberlyst™ 131, Purolite® SGC650, Purolite® C100H, Purolite® C150H, Amberlite® IR 120 and Dowex® 50X8.

Strongly acidic cation exchangers that are particularly preferred according to the invention are the cation exchangers Amberlyst™ 131 and/or Lewatit® K 1221.

A strongly acidic cation exchanger that is very particularly preferred according to the invention is Amberlyst™ 131, which, like the other specified cation exchangers, is commercially available.

To carry out the reaction according to the invention of isoprenol with the aldehyde of the formula (III), the specified starting materials and the selected amount of water, preferably in the form of a mixture, are brought into contact with the selected strongly acidic cation exchanger. The amount of cation exchanger to be used is not critical and can be freely chosen within wide limits taking into consideration the cost and processing aspect. The reaction can accordingly be carried out either in the presence of catalytic amounts or in the presence of large excesses of the selected strongly acidic cation exchanger. Usually, the selected cation exchanger is used in an amount of from about 5 to about 40% by weight, preferably in an amount of from about 20 to about 40% by weight and particularly preferably in an amount of from about 20 to about 30% by weight, in each case based on the sum of isoprenol used and aldehyde of the formula (III). Here, the data refer to the ready-to-use cation exchanger, which is usually pretreated with water and accordingly can comprise amounts of up to about 70% by weight, preferably from about 30 to about 65% by weight and particularly preferably from about 40 to about 65% by weight, of water. Particularly in the case of a discontinuous procedure, an addition of water beyond this may therefore be unnecessary when carrying out the process according to the invention.

The specified strongly acidic cation exchangers can be used either individually or in the form of mixtures with one another in the course of the process according to the invention.

The reaction to be carried out according to the invention can, if desired, also be carried out in the presence of a solvent that is inert under the reaction conditions, such as, for example, tert-butyl methyl ether, cyclohexane, toluene, hexane or xylene. The specified solvents can be used on their own or in the form of mixtures with one another. Within the context of a preferred embodiment of the process according to the invention, the reaction of isoprenol with the selected aldehyde of the formula (III) is carried out without addition of an organic solvent.

The reaction of isoprenol with the selected aldehyde of the formula (III) to be carried out according to the invention in the presence of water and in the presence of a strongly acidic cation exchanger is usually carried out at a temperature in the range from 0 to 60° C., preferably at a temperature in the range from 20 to 60° C. and particularly preferably at a temperature in the range from 20 to 50° C., where the temperature refers to that of the reaction mixture.

The reaction to be carried out according to the invention can, if desired, be carried out discontinuously or continuously. Here, for example in the discontinuous case, the reaction can be undertaken such that a mixture of isoprenol, the selected aldehyde of the formula (III) and water is initially introduced into a suitable reaction vessel and the strongly acidic cation exchanger is added. Following conclusion of the reaction, the cation exchanger can then be separated off from the resulting reaction mixture by suitable separation methods, preferably by filtration or by centrifugation. The order in which the individual reaction components are brought into contact is not critical and can be varied according to the particular processing embodiment.

Within the context of a preferred embodiment, the reaction of isoprenol with the selected aldehyde of the formula (III) to be carried out according to the invention is carried out continuously. For this, for example a mixture of the starting materials isoprenol and aldehyde of the formula (III) to be reacted can be prepared with water and this mixture can be continuously brought into contact with a strongly acidic cation exchanger. For this, the selected cation exchanger can be introduced, for example, into a suitable flow reactor, for example a stirred reactor with inlet and outlet or a tubular reactor, and the starting materials and the water can be discharged continuously into this and the reaction mixture can be continuously discharged. In this connection, the starting materials and the water can, if desired, be introduced into the flow reactor as individual components or else in the form of a mixture as described above.

One preferred embodiment of the process according to the invention accordingly relates to a continuous process for the preparation of 2-substituted 4-hydroxy-4-methyltetrahydropyrans of the formula (I) comprising the steps
    a. providing a flow reactor comprising the selected strongly acidic cation exchanger;
    b. continuously introducing isoprenol, the aldehyde of the formula (III) and water into the flow reactor;
    c. continuously bringing isoprenol, the aldehyde of the formula (III) and water into contact with the strongly acidic cation exchanger in the flow reactor to give a reaction mixture comprising the desired 2-substituted 4-hydroxy-4-methyltetrahydropyrans and
    d. continuously discharging the reaction mixture from the flow reactor.

The selected strongly acidic cation exchanger may be present here either in the form of a loose bed or in the form of a fixed bed in the aforementioned flow reactor.

It is also possible to carry out the reaction of isoprenol with the aldehyde of the formula (III) to be carried out according to the invention in a cascade of a plurality of, for example 2 or 3, successively connected flow reactors, where the individual flow reactors may also be filled with various strongly acidic cation exchangers and if using tubular reactors, these can be operated either in liquid phase mode or trickle mode. Moreover, the reaction mixture discharged from the selected flow reactor can, if desired, also be returned in part back to the continuously operated reaction.

The process according to the invention permits the preparation of 2-substituted 4-hydroxy-4-methyltetrahydropyrans of the formula (I), specifically the preparation of 2-isobutyl-4-hydroxy-4-methyltetrahydropyrans of the formula (I). These are usually produced in the form of reaction mixtures which, besides the desired target compounds, can also comprise radicals of the starting materials used, the water used and also possibly, to a slight extent, also the dehydrated by-products of the formulae (IVa), (IVb) and/or (IVc)

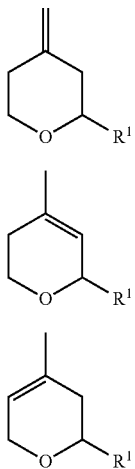

(IVa)

(IVb)

(IVc)

The process according to the invention permits the preparation of the desired hydroxypyrans of the formula (I) or preferably of 2-isobutyl-4-hydroxy-4-methyltetrahydropyran of the formula (Ia) in high yield and high purity, where the undesired dehydration products of the formulae (IVa to IVc) are only produced to a minor extent, if at all.

Further possible by-products which may be mentioned are the acetals of the formula (V)

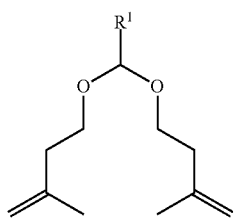

(V)

and the 1,3-dioxanes of the formula (VI)

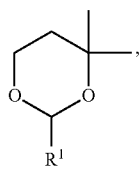

(VI)

where in the case of the reaction of isoprenol with isovaleraldehyde preferred according to the invention, the radical $R^1$ is in each case isobutyl (corresponding to the compounds of the formulae (Va) or (VIa). Just like the unreacted starting compounds and/or the starting compounds used in excess, these by-products can be advantageously returned again to the reaction.

The reaction mixtures obtained according to the invention typically consist to an extent of about 50 to about 90% by weight, often to about 60 to about 80% by weight, of the desired 2-substituted 4-hydroxy-4-methyltetrahydropyrans of the formula (I) and only up to about 20% by weight, preferably only up to about 15% by weight and particularly preferably only up to 10% by weight, of the dehydration products of the formulae (IVa) to (IVc), in each case based on the total weight of the crude product obtained and moreover of the unreacted starting materials and/or starting materials used in excess, and the other specified by-products.

The substance mixtures obtained as crude product can be further purified easily by methods known to the person skilled in the art, in particular by distillation and/or rectification. In this way, the 2-substituted 4-hydroxy-4-methyltetrahydropyran of the formula (I) desired in each case, in particular when using isoprenol and isovaleraldehyde, the desired 2-isobutyl-4-hydroxy-4-methyltetrahydropyran of the formula (Ia), is obtained in a purity of more than 95% by weight or preferably from 97 to 99.9% by weight or particularly preferably from 98 to 99.8% by weight, i.e. in a quality as is required, for example, for use as aroma chemical.

One preferred embodiment of the process according to the invention relates to the preparation of 2-substituted 4-hydroxy-4-methyltetrahydropyrans in the form of mixtures of the cis-diastereomers of the formula (Ib)

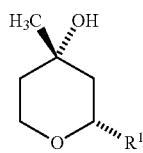

(Ib)

and of the trans-diastereomers of the formula (Ic)

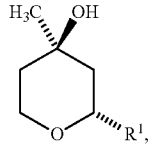

(Ic)

where the diastereomer ratio of the cis-diastereomer of the formula (Ib) to the trans-diastereomer of the formula (Ic) is 65:35 to 95:5, preferably 70:30 to 85:15, and $R^1$ has the meanings given above.

In particular for the reaction of isoprenol with isovaleraldehyde preferred according to the invention, in the course of the process according to the invention 2-isobutyl-4-hydroxy-4-methyltetrahydropyran is obtained in the form of mixtures of the cis-diastereomer of the formula (Id)

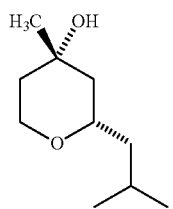

(Id)

and of the trans-diastereomers of the formula (Ie)

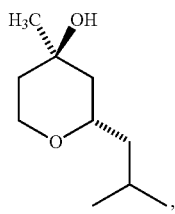
(Ie)

where the diastereomer ratio of the cis-diastereomer of the formula (Id) to the trans-diastereomer of the formula (Ie) is 65:35 to 95:5, preferably 70:30 to 85:15. On account of their particular odoriferous properties, mixtures of this type are suitable to a particular degree for use as aroma chemicals, for example as component with lily of the valley scent for producing fragrance compositions.

The examples below serve to illustrate the invention without limiting it in any way:

Gas chromatographic analyses were carried out in accordance with the following method: 30 m DB-WAX, ID.: 0.32 mm, FD.: 0.25 μm; 50° C., 3° C./min—170° C., 20° C./min to 230° C.—17 min; inj. 200° C., det. 280° C., $t_R$=min; $t_R$ (isovaleraldehyde): 4.1; $t_R$ (dihydropyran isomers of the formulae (IVa) to (IVc)): 10.0; 11.8; 12.3; $t_R$ (isoprenol): 10.6; $t_R$ (1,3-dioxane (Va)): 12.1; $t_R$ (acetal (VIa)): 24.1; $t_R$ (trans-pyranol of the formula (Ie)): 28.2; $t_R$ (cis-pyranol of the formula (Id)): 29.8. Concentrations of the resulting crude products (% by weight) were determined by means of GC analysis using an internal standard.

The water content of the crude products obtained was determined by means of Karl-Fischer titration.

Example 1

An apparatus consisting of a jacketed glass tubular reactor with an internal diameter of 2 cm and a length of 36 cm was filled with 50 g of the strongly acidic cation exchanger Amberlyst™ 131. Prior to use, the cation exchanger was firstly washed several times with water, then once with methanol and finally washed free of methanol using water.

The jacketed glass reactor was filled with a mixture of isovaleraldehyde (112.5 g, 1.31 mol), isoprenol (125 g, 1.45 mol) and 12.5 g of water at room temperature. The reaction solution was circulated for 8 h at a temperature of 40° C. with a circulation volume of 910 ml/h. The jacketed glass reactor was operated at a temperature of 40° C. This gave a crude product in an amount of 250.5 g (yield 73%) with the following composition:
Isovaleraldehyde: 0.56 GC % by weight,
Isoprenol: 2.35 GC % by weight,
Dihydropyran isomers (IVa-c): 9.41 GC area % (GC area %)
1,3-Dioxane (Va): 10.25 GC % by weight,
Acetal (VIa): 0.99 GC area %,
trans-Pyranol (Ie): 17.49 GC % by weight,
cis-Pyranol (Id): 48.28 GC % by weight
Water: 6.9%

Example 2

The jacketed glass reactor was filled with a mixture of isovaleraldehyde (77.4 g, 0.9 mol), isoprenol (86.1 g, 1.0 mol) and 8.6 g of water at room temperature. The reaction solution was circulated for 10 h at a temperature of 25° C. with a circulation volume of 1.5 l/h. The jacketed glass reactor was heated to 25° C. This gave a crude product in an amount of 169.4 g (yield 79%) with the following composition:
Isovaleraldehyde: 0.44 GC area %,
Isoprenol: 3.57 GC area %,
Dihydropyran isomers (IVa-c): 9.76 GC area %,
1,3-Dioxane (Va): 3.16 GC area %,
Acetal (VIa): 0.99 GC area %,
trans-Pyranol (Ie): 18.91 GC % by weight,
cis-Pyranol (Id): 54.13 GC % by weight.

The invention claimed is:

1. A process for the preparation of 2-substituted 4-hydroxy-4-methyltetrahydropyrans of the formula (I)

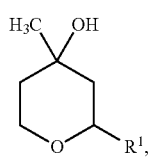
(I)

where the radical
$R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms,
said process comprising reacting 3-methylbut-3-en-1-ol (isoprenol) of the formula (II)

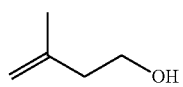
(II)

with an aldehyde of the formula (III)
$R^1$—CHO (III),
wherein the radical $R^1$ has the same meaning as in formula (I) and
wherein the reaction is carried out in the presence of at least 10 mol % water, wherein the amount of water is based on the amount of the 3-methylbut-3-en-1-ol of the formula (II) if the 3-methylbut-3-en-1-ol is used in deficit or to the amount of aldehyde of the formula (III) if used in deficit or, in the case of equimolar reaction of the two starting materials, to the quantitative amount of one of the two, and in the presence of a strongly acidic cation exchanger.

2. The process according to claim 1, wherein the radical $R^1$ is a straight-chain or branched alkyl or alkenyl radical having 1 to 12 carbon atoms, or an optionally alkyl- and/or alkoxy-substituted aryl radical having in total 6 to 12 carbon atoms.

3. The process according to claim 1, wherein the radical $R^1$ is isobutyl.

4. The process according to claim 1, wherein the radical $R^1$ is phenyl.

5. The process according to claim 1, wherein isoprenol and the aldehyde of the formula (III) are used in a molar ratio of from 0.7:1 to 2:1.

6. The process according to claim 5, wherein isoprenol and the aldehyde of the formula (III) are used in a molar ratio of from 1:1 to 1.5:1.

7. The process according to claim 1, wherein the reaction is carried out in the presence of an at least equimolar amount of water, where the amount of water refers to the amount of the starting material isoprenol, used optionally in deficit, or to the aldehyde of the formula (III), or, in the case of the equimolar reaction of the two starting materials, to the quantitative amount of one of the two.

8. The process according to claim 1, wherein a strongly acidic cation exchanger comprising sulfonic acid groups is used.

9. The process according to claim 1, wherein at least one strongly acidic cation exchanger in the H(+) form is used, wherein said cation exchanger comprises a polymer backbone having sulfonic acid groups and is either gel-like or comprises macroporous resins.

10. The process according to claim 9, wherein the ion exchanger is based on a polystyrene backbone with sulfonic acid groups or on a perfluorinated ion exchanger resin with sulfonic acid groups.

11. The process according to claim 1, wherein the reaction is carried out without addition of an organic solvent.

12. The process according to claim 1, wherein the reaction is carried out at a temperature in the range from 20 to 60° C.

13. The process according to claim 1, wherein the reaction is carried out continuously.

14. The process according to claim 13, comprising the steps
   a. providing a flow reactor comprising the selected strongly acidic cation exchanger;
   b. continuously introducing isoprenol, the aldehyde of the formula (III) and water into the flow reactor;
   c. continuously bringing isoprenol, the aldehyde of the formula (III) and water into contact with the strongly acidic cation exchanger in the flow reactor to give a reaction mixture comprising the desired 2-substituted 4-hydroxy-4-methyltetrahydropyrans and
   d. continuously discharging the reaction mixture from the flow reactor.

15. The process according to claim 1, wherein the process produces 2-substituted 4-hydroxy-4-methyltetrahydropyrans in the form of mixtures of the cis-diastereomers of the formulae (Ib)

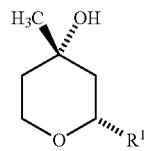

(Ib)

and of the trans-diastereomers of the formula (Ic)

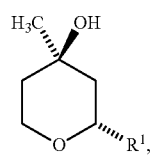

(Ic)

wherein the diastereomer ratio of the cis-diastereomer of the formula (Ib) to the trans-diastereomer of the formula (Ic) is 65:35 to 95:5, and $R^1$ has the meanings given in claim 1.

* * * * *

UNITED STATES PATENT AND TRADEMARK OFFICE
CERTIFICATE OF CORRECTION

PATENT NO. : 8,618,315 B2  Page 1 of 1
APPLICATION NO. : 13/321417
DATED : December 31, 2013
INVENTOR(S) : Gralla et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this
Twenty-second Day of September, 2015

Michelle K. Lee
*Director of the United States Patent and Trademark Office*